US 6,606,568 B2

(12) United States Patent
Meglen et al.

(10) Patent No.: US 6,606,568 B2
(45) Date of Patent: Aug. 12, 2003

(54) METHOD FOR PREDICTING DRY MECHANICAL PROPERTIES FROM WET WOOD AND STANDING TREES

(75) Inventors: Robert R. Meglen, Boulder, CO (US); Stephen S. Kelley, Evergreen, CO (US)

(73) Assignee: Midwest Research Institute, Kansas City, MO (US)

( * ) Notice: Subject to any disclaimer, the term of this patent is extended or adjusted under 35 U.S.C. 154(b) by 267 days.

(21) Appl. No.: 09/738,912

(22) Filed: Dec. 13, 2000

(65) Prior Publication Data

US 2002/0107644 A1 Aug. 8, 2002

Related U.S. Application Data

(60) Provisional application No. 60/214,380, filed on Jun. 28, 2000.

(51) Int. Cl.[7] .............................. G01J 5/02; G06F 19/00
(52) U.S. Cl. .................. 702/30; 250/339.09; 250/339.1
(58) Field of Search ........................ 702/30, 31, 32, 702/42, 43, 40; 250/339.07, 339.09, 339.1, 339.11, 339.12

(56) References Cited

U.S. PATENT DOCUMENTS

| 5,536,942 | A | * | 7/1996 | Barringer et al. ...... 250/339.12 |
| 5,638,284 | A | | 6/1997 | Helmer et al. ......... 364/471.01 |
| 5,680,320 | A | | 10/1997 | Helmer et al. ............... 364/498 |
| 5,680,321 | A | | 10/1997 | Helmer et al. ............... 364/499 |
| 5,965,888 | A | | 10/1999 | Engstrom et al. ...... 250/339.09 |
| 6,175,092 | B1 | * | 1/2001 | Binette et al. ............... 209/587 |
| 6,308,571 | B1 | * | 10/2001 | Stanish et al. ................ 73/597 |
| 6,414,312 | B1 | * | 7/2002 | Nordin et al. ......... 250/339.09 |
| 6,476,915 | B2 | * | 11/2002 | Hartenstein et al. ........ 356/429 |

OTHER PUBLICATIONS

Hoffmeyer, P., et al., Holz als Roh–und Werkstoff 53 (1995) 165–170 (Density and Strength from A Dry Sample).

* cited by examiner

*Primary Examiner*—Patrick Assouad
(74) *Attorney, Agent, or Firm*—Paul J. White

(57) ABSTRACT

A method for determining the dry mechanical strength for a green wood comprising: illuminating a surface of the wood to be determined with light between 350–2,500 nm, the wood having a green moisture content; analyzing the surface using a spectrometric method, the method generating a first spectral data, and using a multivariate analysis to predict the dry mechanical strength of green wood when dry by comparing the first spectral data with a calibration model, the calibration model comprising a second spectrometric method of spectral data obtained from a reference wood having a green moisture content, the second spectral data correlated with a known mechanical strength analytical result obtained from a reference wood when dried and having a dry moisture content.

23 Claims, 7 Drawing Sheets

METHOD FOR PREDICTING DRY MECHANICAL PROPERTIES FROM WET WOOD AND STANDING TREES

This application claims benefit of patent application Ser. No. 60/214,380, filed Jun. 28, 2000.

CONTRACTUAL ORIGIN OF THE INVENTION

The United States Government has rights in this invention pursuant to Contract No. DE-AC36-99GO10337 between the United States Department of Energy and the Midwest Research Institute.

BACKGROUND OF THE INVENTION

1. Field of the Invention

This invention relates to the spectral analysis of wood, and in particular to a method for predicting dry mechanical strength properties from the near infrared (VIS-NIR) spectra (350–2,500 nm) of green wood using a multivariate calibrations model, in follow-up to and based upon provisional application serial No. 60/214,380, filed Jun. 28, 2000.

2. Description of the Prior Art

A method for the nondestructive analysis of the quality and value of a tree, unlike conventional methods, which measure the volume and form of a tree, would provide important information to assist woodland owners in making their thinning decisions, and in the valuation of a stand of timber. The method would also be useful in the analysis of trees or sawn logs, in the woods, for the field sorting of logs to be used as poles, or feedstocks in the manufacture of veneers, lumber or chips, or in the early stages of the wood manufacturing operation.

Visible and near infrared (VIS-NIR) spectroscopy (350–2,00 nm) in combination with multivariate data analysis is currently in use for the characterization of complex systems. These several statistical methods are also termed chemometric methods, forming the discipline of chemometrics, when applied generally to the field of chemistry, and in particular to the field of analytical chemistry. The technique of chemometrics is more fully explained in Brown, S. D., AChemometrics@, Anal. Chem. 62, 84R–101R (1990).

Chemometrics has been described for use in the non destructive analysis of the chemical and physical properties of paper.

For example, U.S. Pat. No. 5,638,284 describes a method for the measurement of the wet strength of paper by analyzing the visible, near-infrared and/or infrared spectrum of the paper/pulp in the process line using a wavelength range within 400 nm to 4000 nm, and applying a chemometric evaluation of the spectrum, to calculate the wet strength of the paper. Other examples include U.S. Pat. No. 5,680,321 (determining physical properties selected from dry tensile strength, hydrophobicity, debonding energy, bursting strength, wettability and printability in paper), and U.S. Pat. No. 5,680,320 (quantifying the amounts of reacted and/or retained chemical additives in paper by analysis of the visible, near-infrared and/or infrared spectrum of the paper/pulp in a process line).

While the foregoing art discloses the use of chemometric evaluation in the analysis of paper products, the mechanical properties of wet-solid-wood samples are much more complex due, in part, to the presence of high concentrations of hemicellulose and lignin in wood relative to these components in paper. The structure and macromolecular morphology of wood, such as roughness, color, and orientation also affect the spectral properties of solid wood. For a wet wood sample, the analysis of these properties are is problematic because moisture in the samples, along with the high concentrations of lignin and hemicellulose tends to block or conceal the spectrometric derived information. Furthermore, many of these paper properties are a direct result of the presence of a small amount of an additive, or size or wet-strength resin, rather than a function of the inherent properties of paper fibers.

One example of the characterization of wood is described in U.S. Pat. No. 5,965,888, in which, NIR spectrometric data are obtained from dried wood chips. The method for the determination of parameters of wood panels comprises analyzing the raw wood chips/panels at a moisture content<10% by a spectrometric method to provide spectral data, and comparing the spectral data with reference spectral data from a reference chip/panel calibrated to known parameters of panels produced from the reference material, or of the reference panel by multivariate analysis. This method is useful in predicting the quality of a dry wood panel based on an analysis of dried wood chips which are used as a feedstock in the manufacturing process.

NIR has also been used for determination of surface roughness and fiber angle of dry wood relative to the duration of the incident light, and for the evaluation of density and the strength of wood from a dry sample. See, e.g., Hoffmeyer, P., et al., Holz als Roh-und Werkstoff 53 (1995) 165–170 (density and strength from a dry sample).

In both U.S. Pat. No. 5,965,888 and Hoffmeyer, P., et al., Holz als Roh-und Werkstoff 53 (1995) 165–170, reference is explicitly made to the problems associated with measuring the NIR properties of wet wood, and seek to overcome them with use of a dry sample for analysis.

However, none of the foregoing references enables prediction of the dry mechanical strength of wet woody biomass, wood fibers, and various composite materials through the use of VIS-NIR measurements of wet wood coupled with a multivariate statistical calibration model. The multivariate statistical calibration model is obtained measuring the modulus of elasticity (MOE) or modulus of rupture (MOR) of the known dry wood and regressing these values against the VIS-NIR spectrum of the wet wood using multivariate techniques. The VIS-NIR spectrum of an unknown wet wood sample can then be input into the calibration model and be used to predict the strength of that piece of wood when it is dried.

A need therefore exists to ascertain any advantages of VIS-NIR spectral sensitivity to simultaneously measure density, moisture content, slope in grain, microfibril angle, and other wood features, which when coupled with multivariate statistical analysis, will correlate the subtle spectral differences between wet wood samples to predict dry wood mechanical properties, such as ultimate bending strength or MOR and MOE.

SUMMARY OF THE INVENTION

One object of the present invention is to provide a method to predict the mechanical strength of dry wood from a wet wood VIS-NIR spectra in a calibration model using multivariate analysis.

Another object of the present invention is to provide a method which is useful in a manufacturing process, for quality control and process monitoring of a feedstock, or product, based on the mechanical properties of dry wood.

A further object of the present invention is to provide a rapid, accurate method for predicting the mechanical properties of standing trees, which is useful in assessing the value of a stand of timber, by quantitatively measuring the quality of the timber.

A still further object of the present invention is to provide a method, which is useful in making timber thinning and harvesting decisions.

An additional object of the present invention is to provide an apparatus for determining the dry mechanical strength of green wood.

The present invention overcomes the problems of the prior art methods by providing a method for predicting the dry mechanical strength for a green wood, comprising: illuminating a surface of the wood to be predicted, the wood having a green moisture content; analyzing the wood surface using a spectrometric method, the method generating a first spectral data; and using a multivariate analysis to predict the dry mechanical strength by comparing the first spectral data with a calibration model, the calibration model comprising a second spectrometric method spectral data obtained from a reference wood, the second spectral data correlated with a mechanical strength analytical result obtained from a reference wood having a dry moisture content.

DESCRIPTION OF THE DRAWINGS

The accompanying drawings, which are incorporated in and which constitute a part of the specification, illustrate at least one embodiment of the invention and, together with the preferred embodiments of the description, establish the principles of the inventive concept.

DESCRIPTION OF THE PREFERRED EMBODIMENTS

Figure 1:
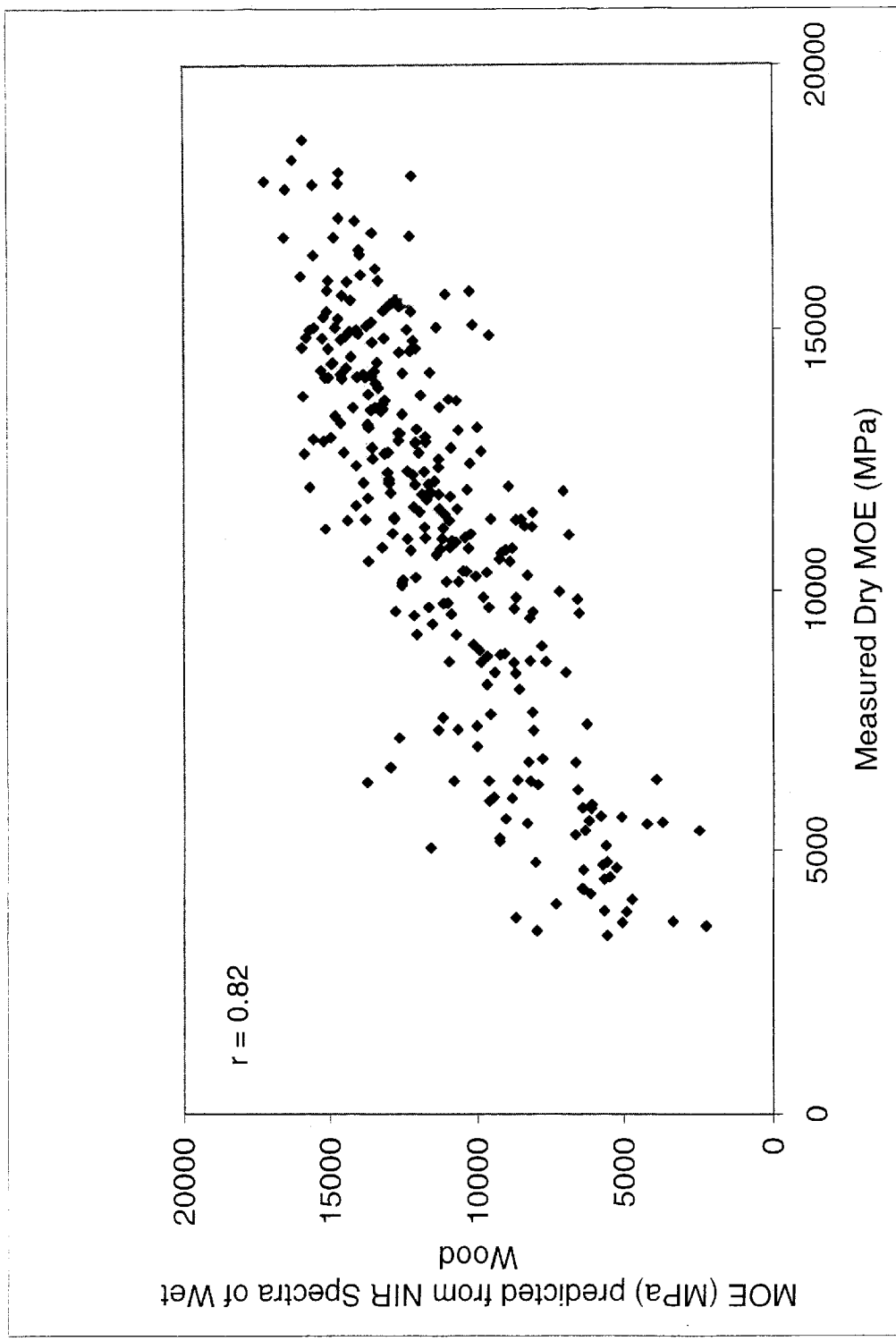
FIG. 1 is a plot of the measured MOE of dry Ponderosa and Lodgepole pines regressed against the MOE predicted by a multivariate calibration model constructed with VIS-NIR spectra taken from wet Ponderosa and Lodgepole pines.

Unless specifically defined otherwise, all technical or scientific terms used herein have the same meaning as commonly understood by one of the ordinary skill in the art to which this invention pertains. Although any methods and materials similar or equivalent to those described herein can be used in the practice of the present invention, the preferred methods and materials are now described.

In general, the present invention provides a VIS-NIR method to predict the mechanical strength of dry processed wood products, e.g., lumber, veneers, flakes, or chips, from wet feedstock and to use this method to predict the strength or value of standing trees and logs, or to improve a process for manufacturing lumber or veneers. For example, the ability to sort wet wood products, based on their dry mechanical properties, would provide for a more efficient use of the resource. In this manner, veneers with high MOE values could be sorted for use as outer plys of a laminated veneer lumber, and veneers having a lower MOE sorted for use as the center ply. Moreover, prediction of the dry strength of a wood product is intended, from the wet VIS-NIR spectra, over a wide range of moisture contents.

It is further intended to predict the strength of wood for standing trees, in situ. VIS-NIR spectra, collected through a fiber-optic probe, are intended for use to predict the dry wood properties from the VIS-NIR spectra of wet wood, in a living tree. This method would allow the development of a commercial system for predicting the strength of standing trees, which should directly translate into increasing their value. Thus, it is intended that presently available portable VIS-NIR systems that can be used in the field would allow a forester to quantitatively measure the quality of a stand of trees. This quantitative measure, along with the volume of the tree, allows the value of that timber stand to be determined. This result is useful in making thinning, harvesting, and timber management decisions.

Woods are classified broadly as softwoods or hardwoods, where softwoods are also known as conifers or evergreens and hardwoods are also known as deciduous or broad-leaved trees. Softwood contains tube-like fibers orientated along the longitudinal axis (grain) and cemented together with lignin. Hardwoods contain more complex structures, such as storage cells, in addition to longitudinal fibers. Fibers in hardwoods are also much smaller and shorter than those in softwoods. Thus, the term "wood" as used herein means either soft or hard wood.

The mechanical properties of woods are influenced by moisture content and grain orientation. (Strengths of dry woods are approximately twice those of wet or green woods. Longitudinal strengths may be as much as 40 times higher than cross-grain strengths.) Moisture content (MC), is defined by the equation MC=(wet weight−oven dry weight)/oven dry weight. In general, wood is considered green if its moisture content is above 19%. Wood is generally considered to be dry when it has reached its equilibrium moisture content, generally between 12% and 15% moisture depending on the relative humidity. Thus, it is understood herein that moisture is not totally absent when used in terms of the expression dry wood.

According to the invention, a sample of wood having unknown mechanical properties and a moisture content greater than 15% is analyzed by a s spectrometric method resulting in spectral data, whereupon said spectral data are compared with a multivariate calibration model comprising reference spectral data from a reference wood material having a moisture content greater than 15% and known dry mechanical properties. The multivariate calibration model contains reference spectral data from the wet wood sample and known analytical results for dry mechanical properties, such as MOE and MOR. The multivariate calibrations models uses techniques such as projection to latent structure or sometimes partial least squares (PLS) modeling to provide a method for rapidly and accurately predicting the dry mechanical strength of the unknown wet wood by means of multivariate analysis.

The present invention demonstrates the utility of using VIS-NIR techniques, coupled with multivariate calibration modeling techniques such as PLS to predict the mechanical properties of wood. The mechanical strength of wood is a complex function of the chemical composition, density, moisture content, slope of grain, microfibril angle of the wood, and other wood features. The mechanical properties of interest desirably include, without limitation, the modulus of elasticity, modulus of rupture, toughness, compression strength, buckling strength, tension strength and stiffness, shear strength, and screw or nail withdrawal load, generally measured, preferably, according to established ASTM standard protocols. Strength and elasticity may be expressed in the units lbf/in2 (multiply lbf/in2 by 6.894 to obtain Kilopascal).

The VIS-NIR spectra simultaneously provide quantitative information on these features. When the VIS-NIR spectra are coupled with analytical techniques such as PLS modeling, these combined techniques give a rapid and accurate method for measuring the mechanical strength of dry wood. The information provided by this technique is useful for decision making in forest harvesting and stand valuation, and in quality control and process monitoring.

This invention may be used as a rapid and accurate method for predicting the strength of standing trees and for predicting the mechanical properties of standing trees and for assessing the value of a stand of timber. Taken in conjunction with conventional measurements of the volume of a tree, this invention is useful to quantitatively measure the quality of the timber. Thus, the method herein may be used as an aid in making decisions, which relate to thinning and harvesting of woodlands. This method can also be used for characterizing the mechanical properties of standing trees or sawn logs, and allocating them for their best use. This method can also be used in controlling a process for manufacturing a wood product or for sorting a feedstock or product.

Either use of the invention requires the production of a calibration model. This calibration model uses a set of "known" samples, which can then be used to predict the mechanical properties of unknown samples of interest. The calibration model requires the VIS-NIR spectra of wet woods samples, drying these samples below 10% moisture content and measuring the mechanical properties of interest. These mechanical properties include but are not limited to modulus of elasticity and modulus of rupture. The objects of the calibration model used in the present invention may be obtained by first analyzing a wet veneer, solid wood sample, tree or log using a fiber-optic probe, located normal to the sample surface, at a distance which provides an observation area in the range of about 0.2 in to 4 ft in diameter. The VIS-NIR reflectance spectra at a wavelength in the range of 350–2500 nm are obtained as an average of 20–100 individual scans. The wet samples may range in moisture content between 19 and 100% and the VIS-NIR spectra are measured on the wet sample. The samples are then dried and may be formed into a shape that allows the mechanical properties to be measured. The mechanical properties of the dry solid wood, including modulus of elasticity, modulus of rupture, toughness, compression strength, buckling strength, tensional strength and stiffness, shear strength, screw or nail withdrawal load are then measured, preferably according to established ASTM standard protocols. The data derived from the wet spectra together with the dry mechanical strength analytical results are preferably input into a computer for use in a calibration model, which uses multivariate analysis to predict the mechanical strength of the dry sample from the wet spectra. Over the entire range of mechanical strengths and moisture contents, the VIS-NIR model is able to provide a very strong correlation between the actual and the predicted mechanical properties. The multivariate analysis of the invention herein may be performed according to the Projection to Latent Structures (PLS), Partial least Squares Regression (PLSR), Principal Component Regression (PCR), Multilinear Regression Analysis (MLR) Principal Component Analysis (PCA), or Discriminate Analysis, but preferably using Projection to Latent Structures. Various programs are available for performing the multivariate analysis herein, including the program The Unscrambler, which is the registered trademark of Camo, Inc., Corvallis, Oreg.

The determination of dry MOE and MOR from a spectrum of an unknown wet solid wood sample by use of the spectrometric measurement comprises two main steps. The calibration model described above provides for the development of calibration or training sets, data processing, and analysis by the use of actual measurements of the spectra for wet samples, bench testing of the actual of interest (MOR and MOE) for the dry samples, and formulation of the calibration model. The second main step is the spectrometric analysis of an unknown wet sample, such as a tree, log, solid wood or veneer, spectral data processing, optionally followed by data analysis, and application of the calibration model, developed in the first main step, to the spectral data obtained from the unknown wet sample. Detailed examples generally relating to the development of a calibration model using multivariate analysis are described in U.S. Pat. Nos. 5,965,888; 5,638,284; 5,680,320; and 5,680,321, the disclosures of which are incorporated herein by reference.

A data output device may, but need not be included in the method of the invention. When used, data output may be according to any means well known, such as a cathode-ray tube, recording instrument, or signal means such as a diode, lamp, or current. For example, an analog to digital or digital to analog converter responsive to a signal, such as a 5 millivolt or other pertinent input or output voltage, may be used in an electrical connection with the invention herein for a direct-digital-control application in a process of sorting a wood product according to its mechanical properties.

The method herein may also be applied in a method for controlling process variables, which influence the strength of a dry solid wood product derived from a raw wet wood feedstock. For example, the present method may be used to determine the mechanical properties, including MOE and MOR, of dry lumber, which information is then fed into a system for controlling the wet feedstock into the process. It is also contemplated in the context of the invention to design a control system in which the obtained spectra optionally, after having reduced noise or base line drift or other manipulation of the spectral data of the wet wood, to input directly into the system for setting the process variable without having translated the spectra into dry strength data. This is suitably accomplished by establishing a calibration model in which process variables are expressed as functions of dry wood strength and the spectral data, and then using the model in the actual production, at which spectral data are obtained from the wet material, and linked with desired dry product structural strength to give a product the necessary quality.

The spectrometric analysis can be performed by an on-line, in-line or at-line optical fiber device to carry the reflected light to the spectrometer, or by taking individual samples for separate analysis. In any case, the spectra are subject to further data treatment to reduce noise or improve the quality of the spectra. It is to be understood that the radiation used in the spectrometric method impinges directly on raw material or the solid wood based sample.

By way of illustration, a device is placed at a distance from the wet sample, containing a light source, detector, electronic components, and other well known components used to transmit a signal through or reflected on or partly through the sample. The resulting signals are returned to the detector in an accompanying optical fiber cable, and recorded.

In a spectrometer, the light is converted into an electric signal which consists of intensity verses wavelength that is then conveyed to a computer, where the spectrum of a previously stored reference sample can be related to the sample spectrum and a reference corrected spectrum is calculated. Correction of the spectrum may be performed by chemometrical methods, well known in the art, such as the description set forth in U.S. Pat. No. 5,638,284, the disclosure of which is incorporated herein by reference. Preferably, a spectrometer having a usable wavelength is the range of 350–2500 nm is used. However, a scanning instrument, a diode array instrument, a Fourier transform instrument or any other similar equipment known in the art, may be used in accordance with the present invention.

An evaluation of wavelengths, which contains absorption or transmission data, provides the relevant features for the analysis. By the application of chemometric methods to the obtained spectra it is possible to ignore wavelengths which do not contain information that contribute to the analysis, even though the measurement will include information from the entire wavelength range.

When used for timber management or harvesting decisions the system may consist of a hand-held device with a fiber optic cable capable of carrying light into the unknown wet wood sample and also carrying the VIS-NIR signal back from the sample. The calibration model for this device is constructed as described above. This device can be hand-held and output to a lamp that is an instantaneous indicator of an analytical result which is useful in assisting the operator in making a timber purchase, thinning, or harvesting decision.

EXAMPLES

The following examples illustrate the manner in which the method in accordance with the present invention can be made and used. In this example, subsamples were taken from short logs, cut from three live pine trees. Trees 1 and 3 were identified as Ponderosa Pine, and tree 2 was identified as a Lodgepole Pine. Two short logs were taken from each tree. One log was taken just above the base of the tree, at about 6 ft, and the second log was taken at about 20 ft, the location for these logs varied slightly to minimize defects within the log. Subsamples measuring between 10 and 24 inches wide and one-quarter inch thick were produced and the VIS-NIR spectra were measured on the wet samples. The subsamples were then dried and the ultimate mechanical properties, e.g., MOE and MOR, were measured on the dry samples. The spectra of the wet samples and the mechanical properties of the dry samples were used to construct a multivariate calibration model that could be used to predict the dry mechanical properties of unknown samples from their wet VIS-NIR spectra. The mechanical properties of both species could be predicted from one PLS model.

In FIG. 1, shows a plot of the measured MOE of dry Ponderosa and Lodgepole pines regressed against the MOE predicted by a multivariate calibration model constructed with VIS-NIR spectra taken from wet Ponderosa and Lodgepole pines.

Figure 2:
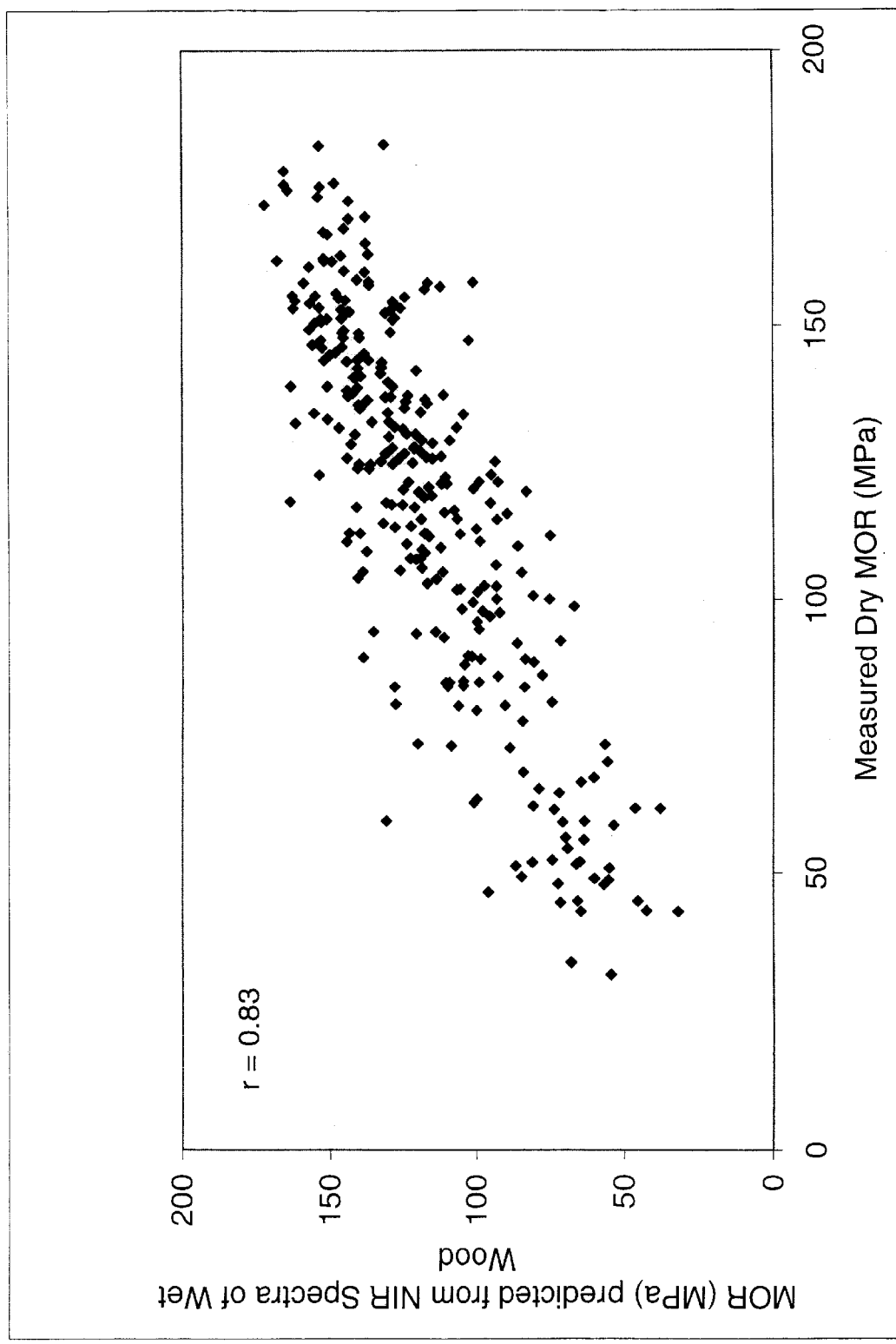
FIG. 2 is a plot of the measured MOR of dry Ponderosa and Lodgepole pines regressed against the MOR predicted by a multivariate calibration model constructed with VIS-NIR spectra taken from wet Ponderosa and Lodgepole pines.

In FIG. 2, shows a plot of the measured MOR of dry Ponderosa and Lodgepole pines regressed against the MOR predicted by a multivariate calibration model constructed with VIS-NIR spectra taken from wet Ponderosa and Lodgepole pines.

Finally, a set of five slash pine trees were harvested. Short logs were cut from four or five locations, approximately every 16 feet, along the height of the trees. VIS-NIR spectra were obtained from holes drilled radially into the logs with a fiber optic device outfitted with a prism that allowed the VIS-NIR beam to be projected at 90° from the axis of the fibers. More than 300 samples were then cut from the wet logs and the VIS-NIR spectra of the wet wood were measured with a fiber optic VIS-NIR system.

Finally, a set of five slash pine trees were harvested. Short logs were cut from four or five locations, approximately every 16 feet, along the height of the trees. VIS-NIR spectra were obtained from holes drilled radially into the logs with a fiber optic device outfitted with a prism that allowed the VIS-NIR beam to be projected at 90° from the axis of the fibers. More than 300 samples were then cut from the wet logs and the VIS-NIR spectra of the wet wood were measured with a fiber optic VIS-NIR system. The samples were then dried and their dry mechanical properties were measured, e.g., MOR and MOE. The spectra of the wet samples and the mechanical properties of the dry samples were used to construct a multivariate calibration model that could be used to predict the dry mechanical properties of unknown samples from their wet VIS-NIR spectra. VIS-NIR spectra from both the probe equipped with the prism to project the VIS-NIR beam at 90° and the VIS-NIR spectra taken directly from the wet surface of the freshly cut sample are used to construct the multivariate calibration model that may be used to predict the dry mechanical properties of unknown samples from their wet VIS-NIR spectra.

Figure 3:
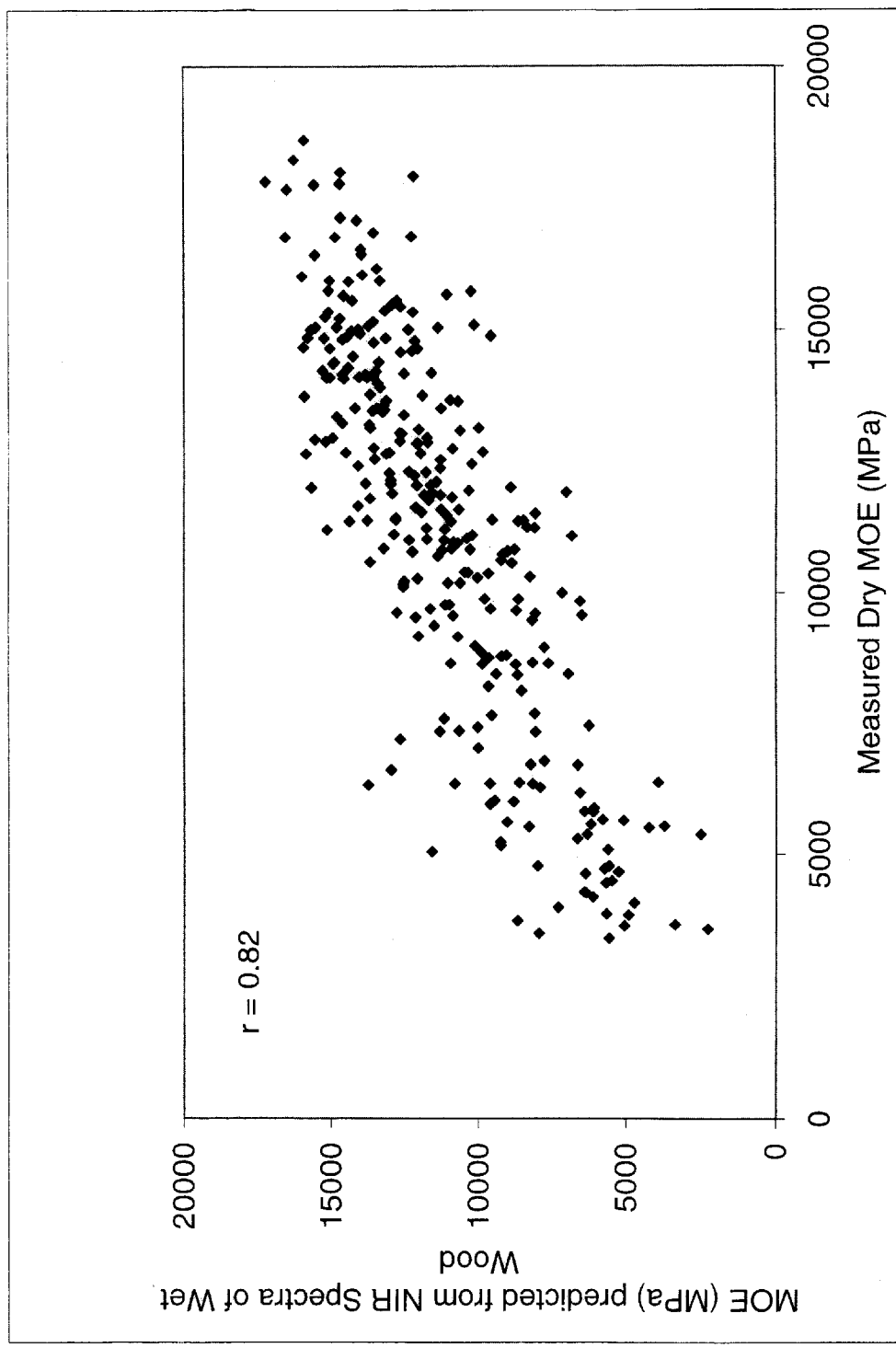
FIG. 3 is a plot of measured MOR of dry Slash pine regressed against the MOR predicted by a multivariate calibration model constructed with VIS-NIR spectra taken from wet Slash pine.

Referring now to FIG. 3, a plot of the measured MOE of dry Slash pine shown as regressed against the MOE predicted by a multivariate calibration model constructed with VIS-NIR spectra taken from wet Slash pine.

Figure 4:
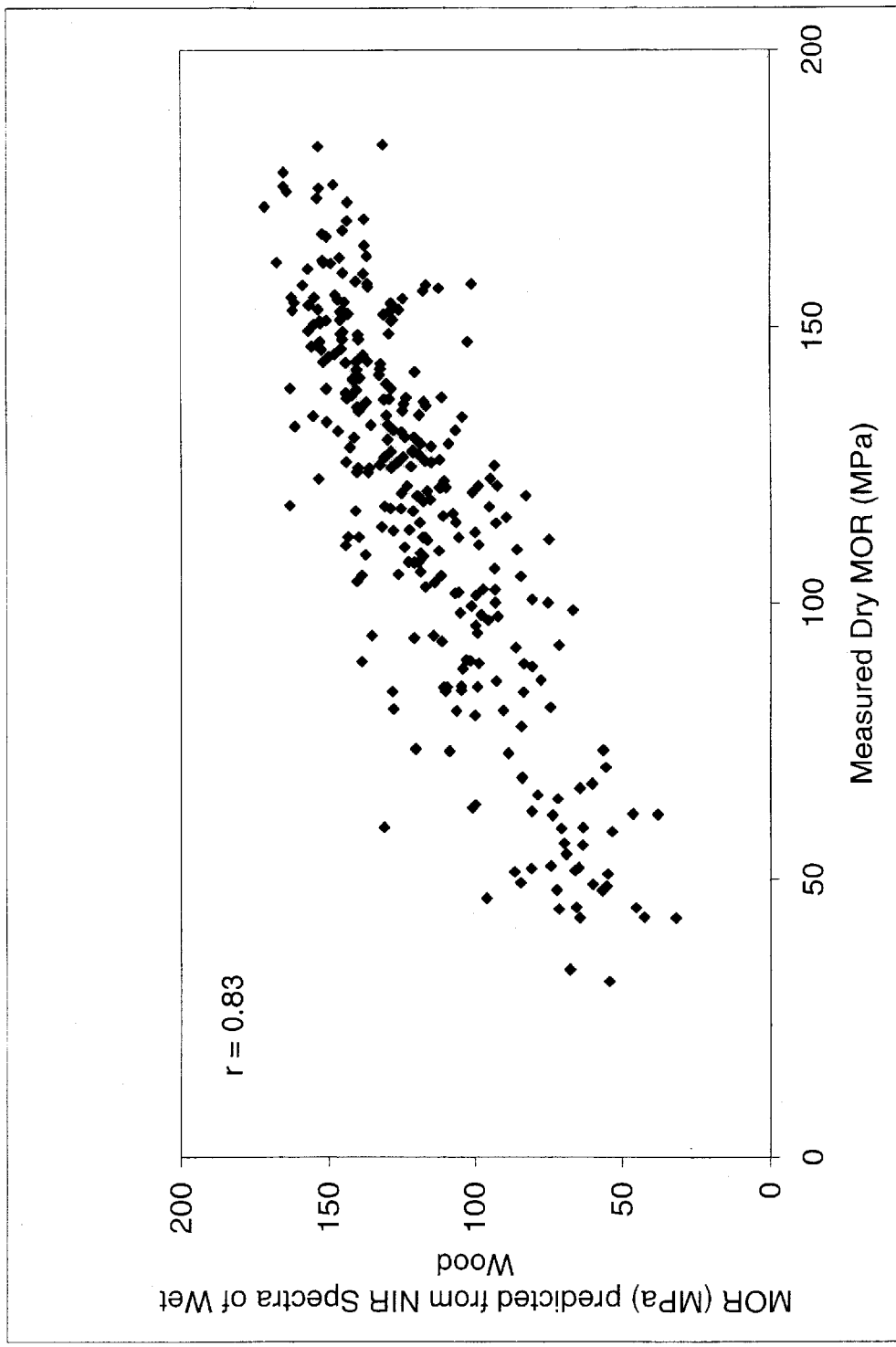
FIG. 4 is a plot of the measured MOE of dry Slash pine regressed against the MOE predicted by a multivariate calibration model constructed with VIS-NIR spectra taken from wet Slash pine.

In FIG. 4, a plot of the measured MOR of dry Slash pine is shown regressed against the MOR predicted by a multivariate calibration model constructed with VIS-NIR spectra taken from wet Slash pine.

The number of data points that are used in the calibration and predictive models described in this invention can be reduced by averaging the spectral data. Averaging the spectral data has several advantages including reducing the computational time for the data processing and analysis, decreasing the cost of the computer used for the data analysis and increasing signal to noise ratio in the spectral data.

TABLE 1

| Wavelength Interval | Mountain Pine (MOE) | Mountain Pine (MOR) | Slash Pine (MOE) | Slash Pine (MOR) |
| --- | --- | --- | --- | --- |
| 1 nm (base case) | 0.88 | 0.88 | 0.82 | 0.84 |
| 2 nm | 0.88 | 0.88 | 0.82 | 0.84 |
| 4 nm | 0.88 | 0.88 | 0.82 | 0.84 |
| 8 nm | 0.87 | 0.87 | 0.81 | 0.83 |
| 16 nm | 0.87 | 0.83 | 0.81 | 0.83 |
| 32 nm | 0.87 | 0.86 | 0.81 | 0.82 |
| 64 nm | 0.86 | 0.87 | 0.78 | 0.82 |

Table 1 shows the results of averaging the spectral data over several different wavelength intervals. All of the spectra were collected between 350 and 2500 nm. It is clear that averaging the spectra over different intervals, up to 32 nm does not have a substantial negative impact on the quality of the correlations. This analysis shows that with the proper data processing and handling the mechanical properties of green wood can be successfully predicted with 20 to 30 individual data points.

Most spectrophotometers include a source, a grating or other means of dispersing light and near infrared energy in a series of monochromatic, single wavelength beams, a suitable photodetector, and computer based controller. The grating may be positioned to provide pre-dispersed monochromatic light first to the sample and then to the detector or, alternatively, polychromatic light from the source may be directed onto the sample and then post-dispersed by the grating before being directed to the detector. Post-dispersion permits analysis of several wavelengths simultaneously.

Figure 5:
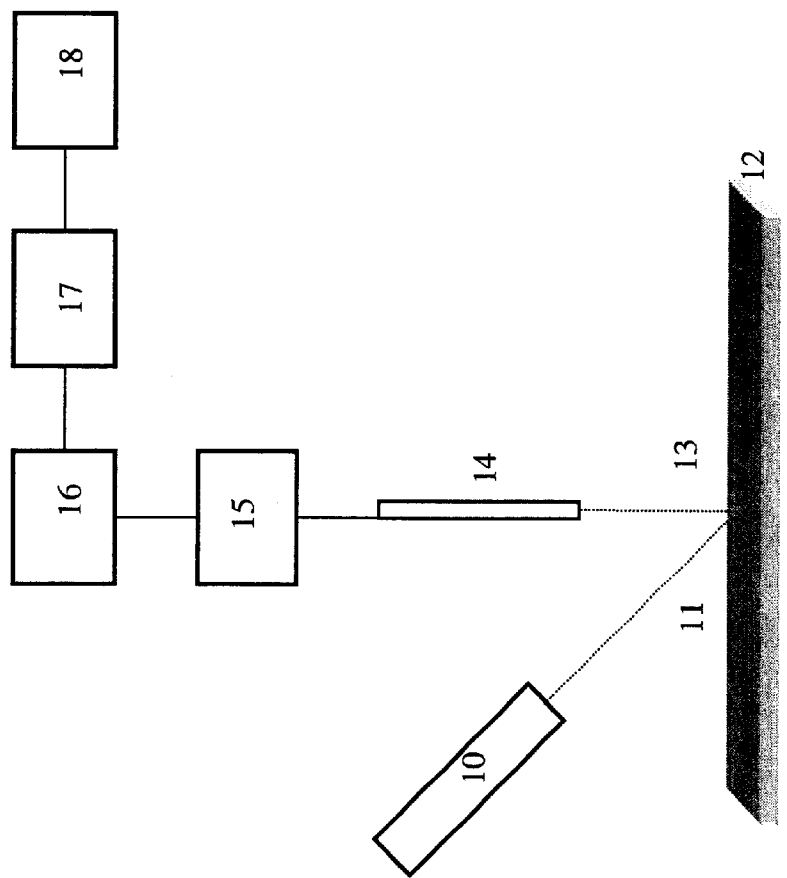
FIG. 5 is a flow chart showing control of the manufacturing process that uses wet wood in the preferred embodiments of the invention.

In the context of the invention, a preferred embodiment used to control the manufacturing process that uses wet wood as the feedstock is shown in FIG. 5. The source 10 is used to illuminate the sample 12. The angle of illumination 11 will depend on the sample geometry and surface roughness, and will range in general from about 20 to about 70 degrees, with 30–40 degrees being preferred. It is also preferred, but not required, that the illumination be parallel to the long axis of the wood fibers. The source can be a common quartz-envelope tungsten-halogen incandescent light, or similar source that delivers a broad spectrum of energy in the range between 350 nm and 2,500 nm. The source can also be a light emitting diode or the output of an acoustical optic tunable filter. The energy can be delivered to the sample by illuminating the sample at a distance of a few inches to several feet, or through an optical fiber or set of optical fibers that is in close contact with the wood sample. When polychromatic light is used for illumination, polychromatic light is reflected back from the sample and passes through a monochromator 15. An optical fiber or set of optical fibers 14 may also collect the reflected polychromatic light. The monochromator or optical fiber or fibers should be oriented above the sample 12 at an angle 13 between about 45 degrees and about 135 degrees, with a preferred angle of 90 degrees.

The monochromator 15 can be one of several designs including a simple grating where the angular motion of the prism or diffraction grating can give a spectrum that is scanned at a known rate over a known time interval. Such a device is referred to as a scanning spectrometer. The monochromator can also be based on a Fourier transform interferometer design where the beam of radiant energy is divided into two or more parts that travel different paths and then recombine to form interference fringes. Acoustical optic tunable filters which are based on a combination of a birefringent crystal and a field oscillating at a specified frequency (which is commonly in the radio frequency range) may also be used. Changes in the frequency of the oscillating field or the composition of the birefringent crystal can change the wavelength of the energy that passes through the acoustical optic tunable filter.

A suitable photodetector 16 will be sensitive in the range of about 350 nm to about 2,500 nm. At the shorter wavelengths of 350 nm to 1,000 nm, the detector can be a photomultiplier or photodiode array detector that, depending on the resolution of the instrument, measures the intensity at each nanometer. At longer wavelengths of 1,000 nm to 2,500 nm, the detectors can be indium gallium arsenic (InGaAs), lead sulfide (PbS) or indium antimonide (InSb) photoconductors.

A computer 17 is used to collect information on the intensities and wavelengths of the reflected radiation at the detector. This information can be displayed on a cathode-ray tube, recording instrument, or signal means such as a diode, lamp, or current. The data may be converted to a form useful for further data processing, in particular data processing techniques that involve multivariate statistical techniques. The output for this statistical analysis may be used as input to an analog to digital or digital to analog converter that is responsive to a signal, such as a 5 millivolt of other pertinent input or output voltage, and may be used in an electrical connection with the invention for a direct-digital-control 18 in the process.

Figure 6:
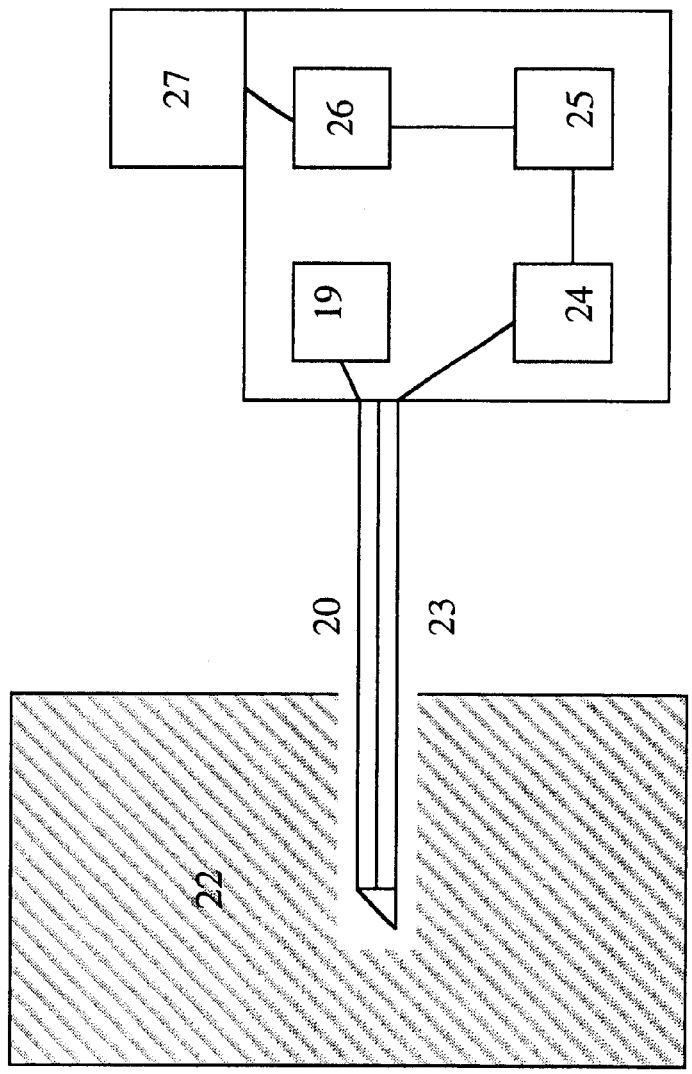
FIG. 6 illustrates a preferred embodiments of the invention for measuring mechanical properties of a standing tree or log.

For measuring the mechanical properties a preferred embodiment of the invention used to measure the mechanical properties of a standing tree or log 21 is shown in FIG. 6. The source 19 is transferred through an optical fiber or group of optical fibers 20 to the sample 22. The source of the illumination can be a common quartz-envelope tungsten-halogen incandescent light, or similar source that delivers a broad spectrum of energy in the range of between 350 nm and 2,500 nm. The source can also be a light emitting diode or the output of an acoustical optic tunable filter. The energy can be delivered to the sample by illuminating the sample at a distance of a few inches to several feet, or through an optical fiber or set of optical fibers that is in close contact or directly on the wood sample. When polychromatic light is used for illumination, polychromatic light is reflected back from the sample and passes through an optical fiber or set of optical fibers 23 to the monochromator 24.

The surface of the tree or log to be illuminated will depend on the nature of the sample and may be either a hole drilled into the tree or log, or a surface reveled by removing the bark of the tree or log. In either case it is preferred to have the illumination on the sides of the wood fibers, generally referred to as the radial or tangential face of the wood in the tree or log. Screening the end of a cut log is also a method of the invention.

The monochromator 24 can be one of several designs including a simple grating where the angular motion of the prism or diffraction grating can give a spectrum that is scanned at a known rate over a known time interval. Such a device is referred to as a scanning spectrometer. The monochromator can also be based on a Fourier transform interferometer design where the beam of radiant energy is divided into two or more parts that travel different paths and then recombine to form interference fringes. Acoustical optic tunable filters, which are based on the combination of a birefringent crystal and a field oscillating at a specified frequency (which is commonly in the radio frequency range) may also be used. Changes in the frequency of the oscillating field or the composition of the birefringent crystal can change the wavelength of the energy that passes through the acoustical optic tunable filter.

A suitable photodetector 25 will be sensitive in the range of about 350 nm to about 2,500 nm. At the shorter wavelengths of 350 nm to 1,000 nm, the detector can be a photomultiplier or photodiode array detector that, depending on the resolution of the instrument, measures the intensity at each nanometer. At longer wavelengths of 1,000 nm to 2,500 nm, the detectors can be indium gallium arsenic (InGaAs), lead sulfide (PbS) or indium antimonide (InSb) photoconductors.

A computer 26 is used to collect information on the intensities and wavelengths of the reflected radiation at the detector. This information may be displayed on a cathode-ray tube, recording instrument, or signal means such as a diode, lamp, or current 27. In the computer 26 the data may be converted to a form useful for further data processing, in particular data processing techniques that involve multivariate statistical techniques. Generally, the output from computer 26 will be processed using a calibration set and a PLS model or some other similar technique, so that the output is a measurement of mechanical or physical features of the sample, rather than the VIS-NIR spectrum. However, the output is based on the VIS-NIR spectrum measured with the photodetector 25.

Figure 7:
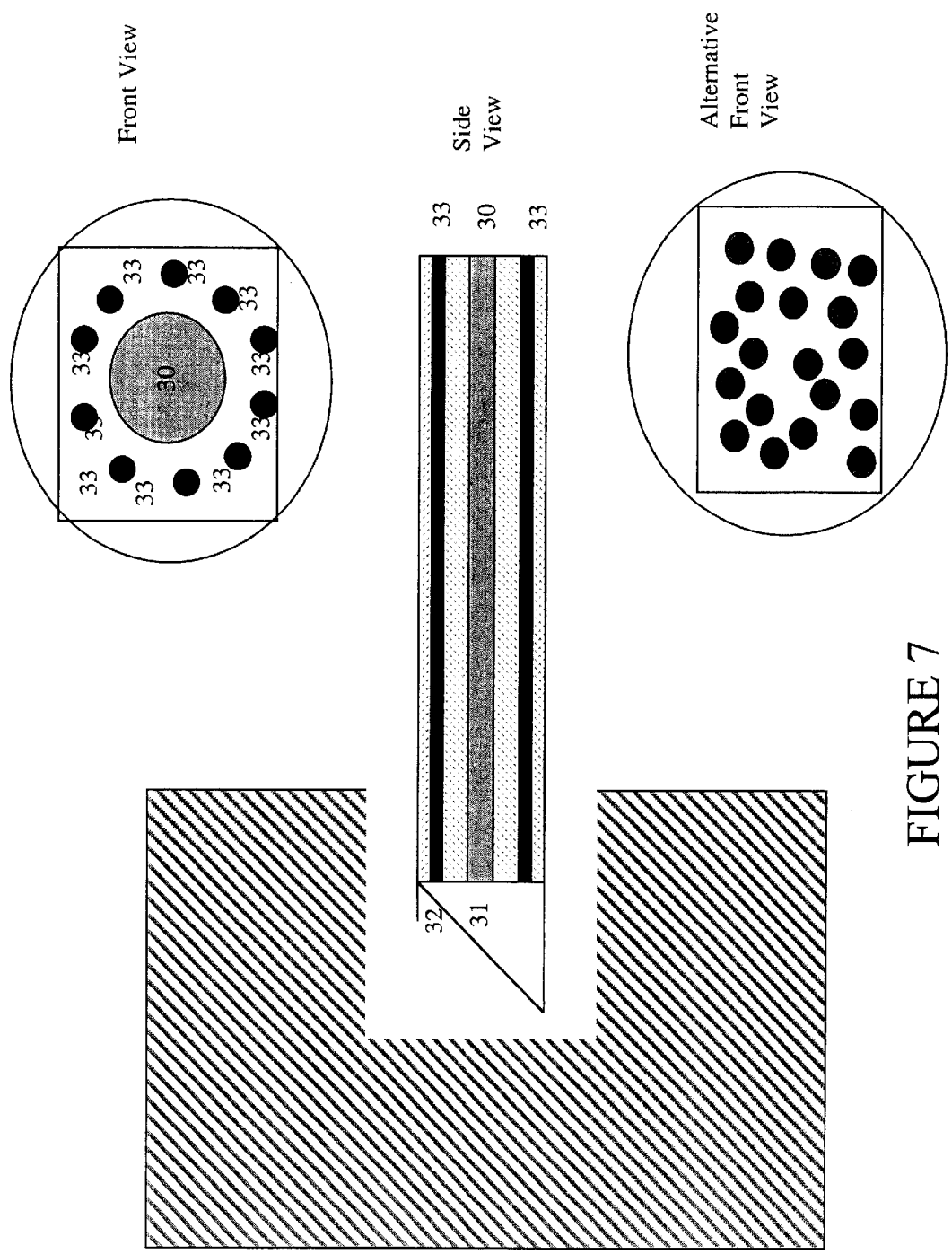
FIG. 7 is a schematic for the design of the probe used for measuring the mechanical properties of a tree or log using a hole drilled into the tree.

FIG. 7 shows a schematic for the design of the probe used for obtaining spectra used for predicting the mechanical properties of a tree or log using a hole drilled into the tree. The source light is carried into the hole in the tree or log by an optical fiber or group of optical fibers 30. The illumination fibers may be randomly spaced in the fiber optic element or made concentric around the observation fiber or fibers. A prism 31 is used to direct a significant portion of the illumination onto the wood fibers, preferably at the radial face or tangential face of the wood fibers. The angle on the face of the prism 32 may vary between 30 and 60 degrees although an angle of 45 degrees is preferred. The source illumination interacts with the wood substrate and a portion is reflected back onto the prism 32 and is passed on to a second optical fiber or set of optical fibers 33. The reflected illumination is then carried back into the spectrometer and processed as shown in FIGS. 5 and 6.

While the present invention has been illustrated and described with reference to particular methods for determining dry mechanical strength for green wood, it will be apparent that modifications can be made therein within the scope of the present invention without departing from the inventive concept, which is defined by the appended claims.

We claim:

1. A method for determining the dry mechanical strength properties of green wood, comprising:
    (a) illuminating a surface of the wood to be determined, said wood having a green moisture content;
    (b) analyzing the surface of said wood using a spectrometric method, the method generating a first spectral data; and
    (c) using a multivariate analysis to predict the mechanical strength of green wood when dry by comparing the first spectral data with a calibration model, said calibration model comprising a second spectrometric method of spectral data obtained from a reference wood having a green moisture content, the second spectral data being correlated with a known mechanical strength analytical result obtained from said reference wood when dried and a having a dry moisture content.

2. The process of claim 1 wherein said green wood is a soft or hard wood.

3. The process of claim 1 wherein said green wood has a moisture content greater than 15 percent weight.

4. The process of claim 1 wherein said green wood has a moisture content greater than 20 percent by weight.

5. The process of claim 1 wherein said dry moisture content is less than 10 percent by weight.

6. The process of claim 1 wherein said dry moisture content is less than 15 percent by weight.

7. The process of claim 1 wherein said reference wood moisture content is in the range of 10 to 100 percent by weight.

8. The process of claim 1 wherein said dry mechanical strength properties are modulus of elasticity, modulus of rupture, toughness, compression strength, buckling strength, tension strength and stiffness, shear strength, and screw or nail withdrawal load.

9. The process of claim 1 wherein said multivariate analysis is selected from Projection to Latent Structures (PLS), Principal Component Analysis (PCA), Partial Least Squares Regression (PLSR), Principal Component Regression (PCR), Multilinear Regression Analysis (MLR) and Discriminant Analysis.

10. The process of claim 1 wherein said green wood is a green feedstock for use in a process having a dry wood lumber, chip, veneer, or flake product.

11. The process of claim 10 further comprising outputting the mechanical strength and using the output in sorting the feedstock relative to the product.

12. The process of claim 10 further comprising outputting the mechanical strength and using the output in sorting the product relative to the feedstock.

13. A method for determining the dry mechanical strength properties of green timber of a standing tree, comprising:
    (a) illuminating a surface of the standing tree, said tree having a green moisture content and analyzing the surface of said tree using a spectrometric method, the method includes a portable instrument means, generating a first spectral data; and
    (b) using a multivariate analysis to predict the mechanical strength of said tree when dry by comparing the first spectral data with a calibration model, said calibration model comprising a second spectrometric method of spectral data obtained from a reference wood having a green moisture content, the second spectral data being correlated with a known mechanical strength analytical result obtained from said reference wood when dried and a having a dry moisture content.

14. The method of claim 13 further comprising outputting the mechanical strength and using the output to identify timber for thinning or harvesting.

15. The process of claim 13 wherein said surface is a hole or cut in said timber and said portable instrument means include a fiber optic probe and a prism assembly, wherein said assembly projects a beam of light at an angle of about 90° incident to a fibrous alignment of sail timber.

16. An apparatus for determining the dry mechanical strength of green wood comprising:
    (a) source means for irradiating a green wood sample with incident radiation containing a spectral region of energy in a range of from about 350 nm to about 2,500 nm in the near-infrared spectrum;
    (b) means for transferring said incident radiation from said source means to a green wood sample;
    (c) return means for carrying reflected radiation from said sample to collecting reflected radiation means;
    (d) photodetector means sensitive to collected reflected radiation in said range of said spectral region of energy;
    (e) computer means to collect intensities and wavelengths of the reflected radiation at said photodetector means to generate a first spectral data; and
    (f) multivariate analysis means to predict the mechanical strength of green wood when dry by comparing said first spectral data with a calibration model, said calibration model comprising a second spectrometric method of spectral data obtained from a reference wood having a green moisture content, the second spectral data being correlated with a known mechanical strength analytical result obtained from said reference wood when dried and having a dry moisture content.

17. The apparatus of claim 16 wherein said means for transferring incident radiation and said means for carrying reflected radiation is an optical fiber or set of optical fibers.

18. The apparatus of claim 17 wherein said collecting reflected radiation means is a monochromator.

19. The apparatus of claim 17 wherein said means for transferring said incident radiation and said means for carrying said reflected radiation comprises prism means disposed about said optical fiber or set of optical fibers in proximity to said green wood sample to direct a portion of said illumination through transferring optical fibers onto wood fibers of said sample and to collect a portion of said reflected radiation through collecting optical fibers.

20. The process of claim 1 wherein said comparison of said first spectral data with said calibration model comprises averaging spectral data including a number of individual data points over predetermined wavelength intervals.

21. The process of claim 20 wherein said number of individual data points can be further reduced by averaging spectral values over several nanometers.

22. The process of claim 21 wherein said averaged spectral range is between 2–16 nm.

23. The process of claim 21 wherein said average spectral range is between 2–64 nm.

* * * * *